United States Patent
Ono et al.

(10) Patent No.: US 8,759,018 B2
(45) Date of Patent: Jun. 24, 2014

(54) METHOD FOR DETERMINING TREATMENT OF DISSEMINATED INTRAVASCULAR COAGULATION

(75) Inventors: Tomoko Ono, Tokyo (JP); Shinichiro Watanabe, Kanagawa (JP); Fumio Furusaki, Tokyo (JP); Ko Igami, Tokyo (JP)

(73) Assignees: Mitsubishi Chemical Medience Corporation, Tokyo (JP); Juridical Foundation the Chemo-Sero-Therapeutic Research Institute, Kumamoto (JP)

( * ) Notice: Subject to any disclaimer, the term of this patent is extended or adjusted under 35 U.S.C. 154(b) by 492 days.

(21) Appl. No.: 13/030,249

(22) Filed: Feb. 18, 2011

(65) Prior Publication Data

US 2011/0143369 A1 Jun. 16, 2011

Related U.S. Application Data

(62) Division of application No. 12/162,879, filed as application No. PCT/JP2007/051489 on Jan. 30, 2007, now abandoned.

(30) Foreign Application Priority Data

Jan. 31, 2006 (JP) .................................. 2006-023596

(51) Int. Cl.
*C12Q 1/56* (2006.01)
*G01N 33/86* (2006.01)

(52) U.S. Cl.
USPC .............. 435/13; 435/7.1; 435/7.4; 435/7.72; 436/16; 436/69; 436/517; 436/811

(58) Field of Classification Search
USPC ........ 435/7, 7.1, 7.92, 7.4, 7.72, 13; 436/506, 436/518, 548, 16, 69, 177, 811, 517
See application file for complete search history.

(56) References Cited

U.S. PATENT DOCUMENTS

2004/0214346 A1 10/2004 Scheiflinger et al.
2005/0186646 A1 8/2005 Cruz (Continued)

FOREIGN PATENT DOCUMENTS

CA 2362483 8/2000
EP 1544293 6/2005

(Continued)

OTHER PUBLICATIONS

Ono et al. Severe secondary deficiency of von Willebrand factor-cleaving protease (ADAMTS 13) in patients with sepsis-induced disseminated intravascular coagulation: its correlation with development of renal failure, Blood, 107 (2): 528-534 (Jan. 15, 2006).*

(Continued)

*Primary Examiner* — Gail R Gabel
(74) *Attorney, Agent, or Firm* — Heslin Rothenberg Farley & Mesiti P.C.

(57) ABSTRACT

A method for determining an appropriate treatment option for a patient who has been diagnosed with disseminated intravascular coagulation (DIC) but who may have thrombotic thrombocytopenic purpura (TTP), by analyzing the amount and/or enzyme activity of a von Willebrand factor (vWF)-cleaving protease (ADAMTS13) and the amount of vWF in a patient that has been diagnosed with DIC is disclosed. Using the method of the present invention, a differential diagnosis of patients with thrombotic thrombocytopenic purpura (TTP) can be made from among patients diagnosed with DIC, which could not previously be distinguished on the basis of only clinical findings or known markers. Also disclosed is a kit for determining an appropriate treatment option, the kit comprising an antibody or a fragment thereof which specifically binds to ADAMTS13.

8 Claims, 5 Drawing Sheets

(56) References Cited

U.S. PATENT DOCUMENTS

| | | |
|---|---|---|
| 2007/0275414 A1 | 11/2007 | Ono et al. |
| 2008/0096221 A1 | 4/2008 | Ono |
| 2009/0220990 A1 | 9/2009 | Igami et al. |

FOREIGN PATENT DOCUMENTS

| | | |
|---|---|---|
| EP | 1568782 | 8/2005 |
| JP | 2006-117537 A | 5/2006 |
| JP | 2006117537 | 5/2006 |
| WO | 0050904 | 8/2000 |
| WO | 2005062054 | 7/2005 |
| WO | 2006049300 | 5/2006 |

OTHER PUBLICATIONS

Coppo (Thrombotic Microangiopathies: Pathophysiology, Diagnosis, Treatment. Reanimation 14 (7): 594-603 (Nov. 2005) Abstract Only.*

Zheng et al., "Structure of von Willebrand Factor-cleaving Protease (ADAMTS13), a Metalloprotease Involved in Thrombotic Thrombocytopenic Purpura", The Journal of Biological Chemistry, vol. 276(44), Nov. 2, 2001, 41059-41063.

Furlan et al., "Deficient Activity of von Willebrand Factor—Cleaving Protease in Chronic Relapsing Thrombotic Thrombocytopenic Purpura", Blood, vol. 89(9), May 1, 1997, 3097-3103.

Ono et al., "Severe secondary deficiency of von Willebrand factor-cleaving protease (ADAMTS13) in patients with sepsis-induced disseminated intravascular coagulation: its correlation with development of renal failure", Hemostasis, Thrombosis, and Vascular Biology, Blood, Jan. 15, 2006, vol. 107(2), 528-534.

Moore, et al., "Decreased von Willebrand factor protease activity associated with thrombocytopenic disorders", Hemostasis, Thrombosis, and Vascular Biology, Blood, Sep. 15, 2001, vol. 98(6), 1842-1846.

Levy et al., "Mutations in a member of the ADAMTS gene family cause thrombotic thrombocytopenic purpura", Nature, vol. 413, Oct. 4, 2001, 488-494.

International Search Report for corresponding International Publication No. WO2007/088849 (PCT Appln. No. PCT/JP2007/051489 filed Jan. 30, 2007).

Ono, Tomoko et al., Presentation No. 0-06 "Development of ELISA for measuring amount of von Willebrand factor-cleaving protease antigen", Japanese Journal of Thrombosis and Hemostasis, vol. 15(5), 2004, p. 421 (Partial Translation).

Ono, Tomoko et al., Presentation No. WS-24-4 "Secondary ADAMTSI3 deficiency in the patients with sepsis-induced DIC", Rinsho Ketsueki, vol. 47(9), 2006, p. 1041 (Partial Translation).

Written Opinion of the International Searching Authority (Form PCT/ISA/237) for corresponding PCT/JP2007/051489. Jan. 30, 2007.

Extended European Search Report for priority application, PCT/JP2007051489. Aug. 5, 2009.

Konetschny et al., "Development of a Highly Sensitive and Specific Enzyme-Linked Immunosorbent Assay for the Detection of ADAMTS-13 in Human Plasma", US, vol. 102(11), Nov. 16, 2003, p. 89b (Abstract).

Obert et al., "Estimation of the von Willebrand Factor-cleaving Protease in Plasma Using Monoclonal Antibodies to vWF", Thrombosis and Haemostasis, vol. 82(5), Nov. 1, 1999, 1382-1385.

* cited by examiner

METHOD FOR DETERMINING TREATMENT OF DISSEMINATED INTRAVASCULAR COAGULATION

CROSS REFERENCE TO RELATED APPLICATIONS

This application is a divisional of co-pending U.S. application Ser. No. 12/162,879, filed Jul. 31, 2008 which is a 371 filing of International Application PCT/JP2007/051489, filed Jan. 30, 2007, published in Japanese on Aug. 9, 2007 as WO 2007/088849, which claims priority to Japanese application no. JP 2006-023596 filed Jan. 31, 2006.

TECHNICAL FIELD

The present invention relates to a method for determining a condition of disseminated intravascular coagulation (hereinafter referred to as DIC).

BACKGROUND ART

In DIC, microthrombi are formed in microvasculature, in the presence of a severe underlying disease. The microthrombi damage the microcirculation and cause organ dysfunction or a bleeding tendency. The following three failures or reactions are observed in DIC:
(1) The microthrombus formation causes a microcirculatory failure, and a variety of organs fall into dysfunction due to ischemia.
(2) The microthrombus formation promotes a consumption coagulopathy, that is, an increase in tissue factor production on the surface of endothelial cells leads to activation of an extrinsic coagulation pathway. Further, coagulation factors and platelets are consumed, and a bleeding tendency occurs.
(3) Hyperfibrinolysis, that is, the fibrinolytic system activated due to the activation of coagulation, generates plasmin, which degrades fibrin. When the $\alpha_2$-plasmin inhibitor ($\alpha_2$PI), which inhibits plasmin, is consumed and decreased to less than 60% of the normal level, fibrin is degraded by the plasmin and a bleeding tendency occurs.

DIC is mainly characterized by the microthrombus formation caused by the abnormal and continuous activation of coagulation, but the fibrinolytic system is also activated. The balance of coagulation and fibrinolysis varies in accordance with underlying diseases or cases. As such cases, a case in which coagulation is remarkably activated, but the fibrinolytic system is suppressed, and a case in which both the coagulation and fibrinolytic systems are remarkably activated, are known. The former is designated coagulation-dominant DIC, and the latter is coagulation-suppressed DIC. Coagulation-dominant DIC is often accompanied by infections, particularly sepsis, and organ failure is often observed as a clinical symptom in patients with coagulation-dominant DIC. In patients with coagulation-suppressed DIC, FDPs (Fibrin degradation products) and PIC (Plasmin/plasmin inhibitor complex), which are fibrinolytic markers, are remarkably increased, and bleeding is often observed. The underlying disease thereof is acute promyelocytic leukemia.

Since a delayed treatment for DIC would directly lead to death, DIC is an urgent disease requiring an early diagnosis and an early treatment. Diagnosis of DIC is now carried out in accordance with the diagnostic criteria for DIC, established by the Ministry of Health and Welfare (Japan). In these diagnostic criteria, DIC is judged by scoring each value of 1) the presence or absence of organ failure, 2) the platelet count, 3) FDPs, 4) fibrinogen, and 5) the PT ratio (prothrombin time ratio). The diagnostic criteria are suitable for a definitive diagnosis of DIC, but are not suitable for an early diagnosis of DIC. Where a clinical treatment of DIC is carried out in accordance with the diagnosis criteria, there are many cases in which DIC is at such an advanced stage that it is too late. Further, there are not a few cases, in the clinical field, where it is difficult to carry out a differentiation as to whether or not a decreased platelet count is caused by DIC. Examples of conditions or diseases with such a decreased platelet count include, for example, a condition accompanied by myelosuppression (such as drugs, viral infections, blood diseases caused dyshemopoiesis, cirrhosis, hepatic insufficiency, thrombotic thrombocytopenic purpura (TTP)/hemolytic uremic syndrome (HUS), and excess pleural effusion or ascites. These conditions or diseases are sometimes accompanied by elevated FDPs and/or elevated D-dimer as well as decreased platelets, and it becomes more difficult to carry out a differentiation of DIC.

As a treatment for DIC, low-molecular-weight heparin or antithrombin III is administered, to suppress the multiple formations of thrombi in blood vessels and inhibit the progression of a consumption coagulopathy. To a patient suffering from coagulation-suppressed DIC, gabexate mesilate having an antithrombin activity and an antifibrinolytic effect is administered. In a patient with DIC accompanied by blood diseases showing a decrease level of the production of platelets, it is essential to replenish platelets by the administration of platelet concentrate. To a patient suffering from DIC with decreased blood fibrinogen, fresh frozen plasma (FFP) is transfused.

A disease condition designated microangiopathic hemolytic anemia (MAHA) is observed in TTP, as well as DIC or HUS. If many microthrombi are formed in blood vessels due to a particular cause, many portions of the microcirculation become narrow. Erythrocytes which forcibly have passed through these narrowed portions are mechanically broken, and hemolysis occurs. These processes are considered the mechanism of the development of MAHA. The main components of the microthrombi, which reduce the internal diameter of the vessels, are fibrin and platelets in DIC and TTP or HUS, respectively.

TTP was first reported in 1924 by Moschcowitz in the United States. TTP is a systemic severe disease which is caused by the clogging of arterioles with platelet aggregates (platelet thrombi), and characterized by the following symptoms: (1) thrombocytopenia (purpura is observed in the skin), (2) microangiopathic hemolytic anemia (caused by the breakdown of erythrocytes), (3) renal failures, (4) fever, and (5) neurologic disturbances.

As a factor of TTP, a cleaving protease specific to plasma vWF as a hemostatic factor (VWF-cleaving protease; VWF-CP), also known as ADAMTS13, was identified. It is known that the amount of ADAMTS13 is significantly lowered in patients with TTP, in comparison with healthy persons (for example, non-patent reference 1, non-patent reference 2, or patent reference 1). If ADAMTS13 is deficient or reduced, unusually large vWF multimers (UL-vWFMs) released from vascular endothelial cells are not cleaved, and an excessive platelet aggregation occurs due to a high shear stress caused in the microcirculation or the like, and as a result, blood vessels are occluded with thrombi.

For example, patent reference 2 discloses a method of detecting thrombosis or the degree of thrombophilia, characterized by measuring ADAMTS13, and acute or chronic myeloid leukemia, acute promyelocytic leukemia, systemic lupus erythematosus, pulmonary embolism, cerebral infarction, veno-occlusive disease, acute lymphocytic leukemia, thrombotic microangiopathy, thrombotic thrombocytopenic purpura, hemolytic uremic syndrome, and deep vein thrombosis are used to exemplify thrombosis. Patent reference 3 discloses a method of detecting platelet thrombosis or organ failure in a patient suffering from DIC or systemic inflammatory response syndrome (SIRS), comprising analyzing ADAMTS13 and/or a cleaving factor thereof (for example, elastase, plasmin, or thrombin).

Further, atypical TTP having a slightly decreased or normal ADAMTS13 activity is known. A variety of causes for atypical TTP were reported, and include congenital factors and acquired factors. An abnormality of genes, such as a plasma Factor H having a complement regulatory activity, or vascular endothelial cell transmembrane protein CD46, were reported as the congenital factors.

TTP is an extremely rare disease, which is generally caused by acquired factors, but rare cases caused by congenital factors are known as described below.

Clinical symptoms in TTP include, for example, diarrhea, abdominal pain, and blood stool due to ischemic enteritis, neurological symptoms such as convulsion and visual disorder, and renal disorder. As laboratory findings, various changes accompanied by hemolysis are observed, for examples, peripheral blood erythrocytes broken by thrombus formation, anemia, decreased platelets, serum LDH (lactate dehydrogenase), elevated indirect bilirubin, or decreased haptoglobin. Elevated serum creatine is observed in patients with renal disorder.

In a treatment for congenital TTP widely used at present, fresh frozen plasma (FFP) is transfused every two or three weeks to replenish ADAMTS13 and maintain a platelet count, i.e., to prevent the development of TTP. A transfusion of platelets is contraindicated in patients with congenital TTP. In approximately one-third of all patients with acquired TTP, an ADAMTS13 activity is remarkably decreased, and almost all the cases are positive for an autoantibody specific to ADAMTS13. Therefore, the administration of FFP alone is insufficient to treat acquired and idiopathic TTP, and a plasma exchange (PE) is the first option. The PE is often carried out together with steroids or a steroid pulse therapy. Of course, a platelet transfusion before the PE is contraindicated. The effects of PE are summarized as 1) the replenishment of ADAMTS13, 2) the removal of an ADAMTS13 inhibitor, 3) the removal of UL-vWFM, and 4) the replenishment of normal vWF necessary for hemostasis. The use of an immunosuppressant, such as vincristine or endoxan, or splenectomy should be considered for intractable cases or repetitive cases. The mortality rate before the introduction of the PE or the FFP transfusion therapy was more than 80%, and the prognosis was very poor. However, such an introduction or a combination thereof with an antiplatelet therapy has remarkably improved the prognosis, so that the survival rate becomes approximately 90% or more now. However, many refractory cases and recurrent cases are known, and there remain problems to be solved. Further, advanced TTP is refractory and has a poor prognosis, and thus, an early diagnosis and an early treatment are necessary.

[non-patent reference 1] Zheng X. et al., J. Biol. Chem., (U.S.A.), 2001, vol. 276, p. 41059-41063

[non-patent reference 2] Furlan M. et al., Blood, (U.S.A.), 1997, vol. 89, p. 3097-3103

[patent reference 1] WO 00/50904

[patent reference 2] WO 2005/062054

[patent reference 3] WO 2006/049300

DISCLOSURE OF THE INVENTION

Problems to be Solved by the Invention

As described above, it was known that patients diagnosed with DIC, based on the diagnostic criteria using known markers and clinical findings, include many cases in which the conditions were not alleviated by the treatment for DIC. With respect to patients with decreased platelets in these cases, it is considered that if the patients were diagnosed with TTP, and treated with an appropriate therapy, such as PE, a prognosis would be favorable. Although a platelet transfusion may be selected as a treatment for DIC, such a platelet transfusion is contraindicated in TTP, even if with remarkably decreased platelets, because the platelet transfusion will aggravate the condition, as described above. Therefore, decreased platelets are observed in both DIC and TTP, but it is desired in the clinical field to clearly distinguish them from each other, so as to carry out an appropriate diagnosis and an appropriate treatment.

The present inventors have conducted intensive studies, and found that a group of patients diagnosed with DIC included a subgroup of patients possibly with acquired TTP, by classifying the patients with DIC according to either the amount (concentration) of ADAMTS13 or enzyme activity of ADAMTS13, or the combination thereof, preferably a combination of the amount (concentration) of ADAMTS13 and/or enzyme activity of ADAMTS13 and the amount (concentration) of vWF. That is, the present inventors differentiated "DIC to be diagnosed as TTP" from "DIC irrelevant to TTP", which could not be differentiated from each other based on clinical findings and known markers, and found that each group of such patients can be treated with a therapy specific to each disease so as to improve the prognosis, and the present invention was completed.

An object of the present invention is to provide a method and kit for differentiating between a patient with TTP and a patient with DIC, which could not be distinguished from each other based on clinical findings and known markers.

Means for Solving the Problems

The object can be solved by the present invention, that is, a method for determining a condition of disseminated intravascular coagulation, characterized by analyzing the amount (concentration) and/or enzyme activity of a von Willebrand factor-cleaving protease (ADAMTS13) in a patient suffering from disseminated intravascular coagulation.

According to a preferred embodiment, the amount (concentration) of a von Willebrand factor (vWF) is further analyzed.

According to another preferred embodiment, the von Willebrand factor-cleaving protease is immunologically analyzed.

Further, the present invention relates to a kit for determining a condition of disseminated intravascular coagulation, comprising an antibody or a fragment thereof which specifically binds to a von Willebrand factor-cleaving protease.

The term "analysis" as used herein includes a detection to determine a presence or absence of a substance (for example, ADAMTS13 or vWF) to be analyzed, and a measurement to quantitatively or semi-quantitatively determine the amount (concentration) or activity of a substance to be analyzed.

Effects of the Invention

DIC and TTP are similar in their conditions, and thus, are difficult to accurately diagnose. Further, in both cases, if an appropriate treatment determined by an early diagnosis is not carried out at an early stage, the patient will die, and therefore, it is very important to differentiate "DIC to be diagnosed as TTP" from "DIC irrelevant to TTP". According to the present invention, in patients diagnosed with DIC based on the present diagnosis criteria, "DIC to be diagnosed as TTP" can be differentiated from "DIC irrelevant to TTP", and an appropriate treatment can be carried out to elevate the survival rate or reduce the mortality rate.

BEST MODE FOR CARRYING OUT THE INVENTION

[1] Determination Method of the Present Invention

In the method of the present invention, the condition of DIC can be determined by analyzing at least one (preferably both) of the amount (concentration) of ADAMTS13 and/or the enzyme activity of ADAMTS13, or using a combination of the amount (concentration) of vWF and at least one (preferably both) of the amount (concentration) of ADAMTS13 and/or the enzyme activity of ADAMTS13, in a patient with DIC.

The term "to determine a condition of DIC" as used herein includes to determine various conditions in a patient suffering from DIC, which are useful for the decision of an appropriate treatment, for example, to select patients to be accurately diagnosed with TTP, and to be treated with another therapy, from among patients diagnosed with DIC, that is, to differentiate between "DIC to be diagnosed as TTP" and "DIC irrelevant to TTP". Further, the term "to determine a condition of DIC" as used herein further include a decision and a prediction on the basis of the determination of the conditions, for example, a determination of an appropriate treatment, a prognosis, and a monitoring.

In the method of the present invention, a differential diagnosis between "DIC possible to be TTP" and "DIC irrelevant to TTP" can be carried out by using, as an index, for example, the difference in the amount (concentration) and/or enzyme activity of ADAMTS13 in a patient with DIC. Further, with respect to patients who are difficult to diagnose and are contained in a DIC patient group, the DIC patient group can be categorized, by using as an index a combination of the amount (concentration) and/or enzyme activity of ADAMTS13 and the amount (concentration) of vWF [for example, a ratio of the amount of vWF to the amount (concentration) and/or enzyme activity of ADAMTS13], into, for example, three subgroups to differentiate "DIC to be diagnosed as TTP" from "DIC irrelevant to TTP", and thus, an appropriate therapy specific to each patient can be proposed. As an index for categorization, thresholds of the amount (concentration) of ADAMTS13 and ADAMTS13 activity may be selected.

The term "von Willebrand factor-cleaving protease (vWF-cleaving protease)" as used herein means a metalloprotease, sometimes referred to as ADAMTS13, which specifically cleaves the von Willebrand factor (VWF) at the bond between tyrosine (842) and methionine (843) contained in an A2 domain thereof.

It is known that the amount of ADAMTS13 is significantly decreased in patients with TTP in comparison of healthy persons [for example, Zheng X. et al., J. Biol. Chem., (U.S.A.), 2001, vol. 276, p. 41059-41063; Furlan M. et al., Blood, (U.S.A.), 1997, vol. 89, p. 3097-3103; and WO 00/50904]. Ono et al. reported that the amount of ADAMTS13 was significantly decreased in DIC patients with a variety of underlying diseases but diagnosed based on the DIC score, in comparison with healthy persons, and that amounts of ADAMTS13 in a group of patients diagnosed with TTP were 5% to 45%, and amounts of ADAMTS13 in a group of DIC patients ranged from 10% to 95% [Ono T. et al., The Japanese Society on Thrombosis and Hemostasis, 2004 (Abstracts were published on October 1.)].

Further, many observations on ADAMTS13 in various diseases have recently been reported, and whereas it was considered that ADAMTS13 activity was remarkably decreased in TTP patients, it was reported that ADAMTS13 activity was not remarkably decreased in 60% of TTP patients (Masanori Matsumoto, Vascular Biology & Medicine, 2005, vol. 6, p. 65-72).

However, it has not been reported that "DIC to be diagnosed as TTP" can be differentiated from "DIC irrelevant to TTP" in patients diagnosed with DIC by using only ADAMTS13.

A subject (a person to be diagnosed) to whom the method of the present invention may be applied is a DIC patient. A preferred sample to be assayed is, for example, blood such as plasma or a serum. Examples of samples other than blood include various body fluids, such as cell or tissue fluids, lymph, a thymic fluid, an ascites fluid, an amniotic fluid, gastric juices, urine, pancreatic juices, spinal fluid, and saliva. The plasma is preferably citrated plasma or heparinized plasma.

In the method of the present invention, a determination of a condition of DIC and a decision of appropriate therapy can be carried out by collecting samples from DIC patients and TTP patients, measuring the concentration of ADAMTS13, ADAMTS13 activity, and/or the concentration of vWF, and comparing the measured values. To distinguish DIC patients possibly with TTP from other DIC patients, it is preferable to have previously determined various thresholds for judgment, such as thresholds for the concentration of ADAMTS13 and ADAMTS13 activity, and a threshold for a ratio of vWF to concentration or activity of ADAMTS13, by using samples collected from TTP patients.

As shown in Examples described below, the following categorization can be, for example, carried out.

First, patients in which two or three items from among the following items 1) to 3) apply are categorized into a "group of DIC patients who possibly to suffer from TTP (group A)", and the others were categorized into a "group of DIC patients who do not possibly to suffer from TTP (group B)".

1) The amount (hereinafter referred to as Aag) of ADAMTS13 is, for example, 30% or less.
2) The activity (hereinafter referred to as Aact) of ADAMTS13 is, for example, 15% or less.
3) The ratio (Aact/Aag) of the amount of ADAMTS13 to the ADAMTS13 activity, for example, is 2.0 or more. These patient groups (group A and group B) may be further categorized, on the basis of a ratio (Vag/Aag) of the amount of vWF (hereinafter referred to as Vag) to the amount of ADAMTS13 (Aag) and a ratio (Vag/Aact) of the amount of vWF to the ADAMTS13 activity (Aact), into the following three groups:

Group 1: Vag/Aag is, for example, 8 or more, and Vag/Aact is, for example, 16 or more.
Group 2: Vag/Aag is, for example, 8 or less, and Vag/Aact is, for example, 16 or more.
Group 3: Other than groups 1 and 2 (i.e., Vag/Aact is, for example, less than 16.)

As shown in Examples described below, two patients diagnosed with TTP were categorized into Group 1. Further, as shown in Examples, among Group 1 to Group 3, Group 1 and Group 2 are a "group of DIC patients to be diagnosed with TTP", and Group 3 is a "group of DIC patients irrelevant to TTP".

The above values Aag, Aact, and Vag are relative values to normal values, and the above ratios (Aact/Aag, Vag/Aag, and Vag/Aact) are calculated from these relative values.

When thresholds for judgment have previously been determined, measured values obtained from a subject whose condition is to be predicted are used to analyze Aag and/or Aact, or Aag and/or Aact and Vag (such as Vag/Aag and/or Vag/Aact), and then, the above judgment and/or prediction can be carried out for the subject. The thresholds for judgment are considered to depend on various conditions, such as an underlying disease, sex, or age. However, those skilled in the art can easily determine the normal ranges or the thresholds for judgment, by selecting an appropriate statistical population corresponding to the subject(s) and statistically processing data obtained from that population.

In the method of the present invention, a method of analyzing the concentration of ADAMTS13 is not limited, so long as an amount of ADAMTS13 may be quantitatively or semi-quantitatively determined, or a presence or absence of ADAMTS13 may be judged, by the analyzing method. Examples of the analyzing method include an immunological method using an anti-ADAMTS13 antibody or a fragment thereof (such as an enzyme-linked immunosorbent assay, a latex agglutination assay, a chemiluminescence immunoassay, a fluorescent antibody method, a radioimmunoassay, immunoprecipitation, immunohistochemical staining, or Western blotting), a biochemical method (such as an enzyme assay), and a molecular biological method for measuring an mRNA.

When an immunological method is used in analyzing ADAMTS13, an anti-ADAMTS13 antibody may be prepared in accordance with a known method, such as a method described in WO 2004/029242. Each immunoassay may be carried out in accordance with, for example, WO 2004/029242.

As a method of measuring a concentration of ADAMTS13, an immunological method is preferable from the viewpoint of sensitivity and convenience. The immunological method means a method of analyzing ADAMTS13 by an ELISA method, a latex method, or immunochromatography, using an antibody against ADAMTS13. As the immunological method, there may be mentioned, for example, a competition method using a labeled ADAMTS13, a sandwich method using a labeled antibody, a latex bead method in which an agglutination of beads coated with an antibody is observed, and a method using an antibody conjugated to a colored particle such as gold colloid. Any method using the antibody against ADAMTS13 is included in preferred embodiments of the present invention. The antibody may be monoclonal or polyclonal. An antibody fragment, such as Fab, Fab', F(ab')$_2$, or Fv, may be used.

The enzyme activity of ADAMTS13 may be measured by, for example, a method utilizing an SDS-agarose electrophoresis [Furlan M. et al., Blood, (U.S.A.), 1997, vol. 89, p. 3097-3103]; an ELISA method using a recombinant antigen of the A2 domain of vWF, as a substrate of vWF [Whitelock J L et al., Journal of Thrombosis and Haemostasis, (United Kingdom), 2004, vol. 2, p. 485-491]; or a method using a quenched fluorescent substrate FRETS-VWF73, prepared by introducing a fluorescent group [2-(N-methylamino)benzoyl, Nma] and a quenching group (2,4-dinitrophenyl, Dnp) into a synthetic peptide corresponding to 73 residues of ASP1596-Arg1668 located in the A2 domain of vWF, as a substrate of the vWF cleaving protease [Kokame K. et al, British Journal of Haematology, (United Kingdom), 2005, vol. 129, p. 93-100]. Further, a method described in the specification of Japanese Patent Application No. 2005-148793, that is, an analyzing method comprising the steps of (1) in a liquid, bringing a sample possibly containing ADAMTS13 into contact with an immobilized substrate prepared by binding vWF or a fragment thereof to an insoluble carrier, (2) separating the liquid from the insoluble carrier, and (3) analyzing the vWF or the fragment thereof which remains in the insoluble carrier, and/or a vWF fragment which is released from the insoluble carrier and is contained in the liquid, may be used.

The concentration of vWF may be measured by, for example, a method of measuring an activity by utilizing an aggregation activity of human platelets and a ristocetin cofactor [Allain J P et al., J. Lab. Clin. Med., (U.S.A.), 1975, vol. 85, p. 318-328]; or an immunoassay using an anti-vWF antibody [Brown J E et al., Thromb. Res., (U.S.A.), 1986, vol. 43, p. 303-311]. The immunoassay is preferable from the viewpoint of sensitivity and convenience.

[2] Determination Kit of the Present Invention

The kit of the present invention comprises at least an anti-ADAMTS13 antibody or a fragment thereof. It is preferable that the kit of the present invention comprises two or more types of anti-ADAMTS13 antibodies. The anti-ADAMTS13 antibody may be a monoclonal antibody or a polyclonal antibody. When two or more types of anti-ADAMTS13 antibodies are contained, one of the antibodies may be labeled as a second antibody, or a labeled anti-second-antibody antibody may be further added to the kit.

EXAMPLES

The present invention now will be further illustrated by, but is by no means limited to, the following Examples.

Example 1

Measurements of Coagulation and Fibrinolysis Marker Levels in Patients with DIC and Patients with TTP Samples of 3.8% citrated plasma were collected from patients with DIC (n=23) and patients with TTP (n=2). Marker levels except for a platelet count were measured with LPIA-NV7 (Mitsubishi Kagaku Iatron) using commercially available kits (LPIA series; Mitsubishi Kagaku Iatron). Samples of 3.2% citrated plasma were collected, and a platelet count was measured with KX-21 (Sysmex).

The results of the measurements are shown in Table 1. In Table 1, PAI-1 means a plasminogen activator inhibitor-1, D-D means D-dimer, Fbg means fibrinogen, FDP-P means plasma FDPs, PLT means platelets, and TAT means a thrombin/antithrombin III complex. The patients diagnosed with DIC included patients with a remarkably decreased platelet count, but these patients could not be distinguished from patients with TTP, based on only conventional coagulation and fibrinolysis marker levels.

TABLE 1

| | Diagnosis | PIC µg/mL | PAI-1 ng/mL | D-D µg/mL | Fbg mg/dL | FDP-P ng/mL | PLT ×10$^4$/µL | TAT ng/mL |
|---|---|---|---|---|---|---|---|---|
| Patient 1 | TTP | 1.1 | 39.7 | 3.6 | 204 | 2.5 | 2.0 | — |
| Patient 2 | TTP | 4.2 | 10.7 | 6.7 | — | — | 0.9 | — |
| Patient 3 | DIC | 4.9 | 924.5 | >2000 | 197 | 261.5 | 1.2 | 48.1 |
| Patient 4 | DIC | 2.0 | 55.7 | 1000-2000 | 445 | 64.1 | — | 5.6 |
| Patient 5 | DIC | 2.4 | 220.7 | >2000 | 838 | 49.2 | 0.5 | 12.9 |
| Patient 6 | DIC | 1.3 | 70.4 | 500-1000 | 433 | 27.5 | — | 3.4 |
| Patient 7 | DIC | 3.0 | 25.2 | 1000-2000 | 413 | 17.9 | — | — |
| Patient 8 | DIC | 4.4 | 228.3 | 33.7 | 26 | 189.0 | — | 57.4 |
| Patient 9 | DIC | 0.6 | 40.1 | <200 | 703 | 4.5 | — | 1.2 |
| Patient 10 | DIC | 1.0 | 28.1 | 12.1 | 165 | 24.8 | — | 7.6 |
| Patient 11 | DIC | 0.5 | 69.4 | <200 | 360 | 2.7 | — | 1.4 |
| Patient 12 | DIC | — | 25.6 | 1.1 | 388 | 3.4 | — | — |
| Patient 13 | DIC | 0.7 | — | 1.5 | 194 | 1.7 | — | 1.9 |
| Patient 14 | DIC | 4.6 | 105.6 | >2000 | 423 | 24.1 | 10.4 | 32.5 |
| Patient 15 | DIC | 1.1 | 29.1 | 500-1000 | 401 | 6.7 | — | 1 |
| Patient 16 | DIC | 4.1 | 178.0 | >2000 | 176 | — | 13.4 | 7.6 |
| Patient 17 | DIC | 1.3 | 16.2 | 2.1 | 680 | 9.8 | — | 2 |
| Patient 18 | DIC | 6.7 | 31.6 | >2000 | 342 | 59.9 | 3.5 | 4.4 |
| Patient 19 | DIC | 0.7 | 23.8 | <200 | 416 | 2.0 | — | 1.4 |
| Patient 20 | DIC | — | 1091.2 | 15.0 | 432 | 13.7 | 0.2 | — |
| Patient 21 | DIC | 3.4 | 53.5 | 1000-2000 | 260 | 15.7 | 1.8 | 9.6 |
| Patient 22 | DIC | — | 162.2 | 200-500 | 307 | 5.7 | 22.9 | — |
| Patient 23 | DIC | — | — | >2000 | 632 | 51.0 | 25.4 | — |
| Patient 24 | DIC | 31.6 | 17.9 | 22.1 | 126 | 55.9 | 1.1 | — |
| Patient 25 | DIC | 7.6 | 22.4 | 33.8 | 340 | 28.9 | 5.2 | — |

Example 2

Analysis of Amount of ADAMTS13 Antigen, Enzyme Activity of ADAMTS13, and Amount of vWF Antigen in Patients with DIC and Patients with TTP Samples of 3.8% citrated plasma were collected from healthy persons (n=12), patients suffering from DIC (n=23) and patients suffering from TTP (n=2). In this regard, the DIC patients were diagnosed with DIC in accordance with the diagnostic criteria for DIC as described above, and the TTP patients were diagnosed with TTP in accordance with clinical findings. The amount (Aag) of an ADAMTS13 antigen was determined using a commercially available kit (ADAMTS-13 ELISA kit; Mitsubishi Kagaku Iatron). The enzyme activity (Aact) of ADAMTS13 was determined by an SDS-agarose gel electrophoresis [Furlan M. et al., Blood, (U.S.A.), 1997, vol. 89, p. 3097-3103]. The amount (Vag) of a vWF antigen was determined using a commercially available kit (STA LIAtest: Roche Diagnostics).

The results of the measurements are shown in Table 2. In Table 2, Aag and Aac are indicated as a percentage with the average of values obtained in healthy persons (n=12) regarded as 100%. Vag is indicated as a percentage to the standard (normal person) contained in the kit.

TABLE 2

| | | Diagnosis | Aag % | Aact % | Aag/Aact | Vag % | Vag/Aag | Vag/Aact | Category |
|---|---|---|---|---|---|---|---|---|---|
| Group possibly with TTP | Patient 1 | TTP | 14.3 | 3.0 | 4.8 | 125.5 | 8.7 | 41.8 | TTP |
| | Patient 2 | TTP | 32.2 | 15.1 | 2.1 | 340.8 | 10.6 | 22.5 | |
| | Patient 3 | DIC | 17.3 | 6.8 | 2.5 | 214.7 | 12.4 | 31.4 | Group 1 |
| | Patient 4 | DIC | 12.3 | 7.9 | 1.6 | 195.2 | 15.9 | 24.7 | |
| | Patient 5 | DIC | 8.9 | 9.4 | 1.0 | 170.0 | 19.0 | 18.1 | |
| | Patient 6 | DIC | 8.3 | 3.0 | 2.8 | 175.5 | 21.1 | 58.5 | |
| | Patient 7 | DIC | 21.9 | 3.0 | 7.3 | 237.0 | 10.8 | 79.0 | |
| | Patient 8 | DIC | 24.4 | 8.8 | 2.8 | 210.8 | 8.6 | 23.9 | |
| | Patient 9 | DIC | 56.0 | 3.0 | 18.7 | 271.8 | 4.9 | 90.7 | Group 2 |
| | Patient 10 | DIC | 42.3 | 6.2 | 6.9 | 239.8 | 5.7 | 38.9 | |
| | Patient 11 | DIC | 28.7 | 8.8 | 3.3 | 182.4 | 6.4 | 20.7 | |
| | Patient 12 | DIC | 44.0 | 15.0 | 2.9 | 216.9 | 4.9 | 14.4 | Group 3 |
| | Patient 13 | DIC | 35.7 | 12.8 | 2.8 | 180.7 | 5.1 | 14.1 | |
| | Patient 14 | DIC | 24.6 | 10.8 | 2.3 | 140.8 | 5.7 | 13.1 | |
| Group irrelevant to TTP | Patient 15 | DIC | 76.5 | 94.4 | 0.8 | 56.6 | 0.7 | 0.6 | |
| | Patient 16 | DIC | 59.0 | 107.1 | 0.6 | 124.7 | 2.1 | 1.2 | |
| | Patient 17 | DIC | 72.0 | 53.1 | 1.4 | 169.0 | 2.3 | 3.2 | |
| | Patient 18 | DIC | 41.7 | 20.9 | 2.0 | 111.4 | 2.7 | 5.3 | |
| | Patient 19 | DIC | 61.7 | 59.4 | 1.0 | 218.4 | 3.5 | 3.7 | |
| | Patient 20 | DIC | 56.2 | 75.0 | 0.7 | 214.8 | 3.8 | 2.9 | |
| | Patient 21 | DIC | 35.2 | 20.9 | 1.7 | 161.2 | 4.6 | 7.7 | |
| | Patient 22 | DIC | 41.1 | 19.5 | 2.1 | 198.9 | 4.8 | 10.2 | |
| | Patient 23 | DIC | 23.7 | 33.3 | 0.7 | 186.8 | 7.9 | 5.6 | |
| | Patient 24 | DIC | 79.5 | 83.5 | 1.0 | 172.7 | 2.2 | 2.1 | |
| | Patient 25 | DIC | 77.3 | 67.9 | 1.1 | 226.0 | 2.9 | 3.3 | |
| | Healthy 1 | | 102.1 | 100 | 1.0 | 80.2 | 0.8 | 0.8 | Healthy |
| | Healthy 2 | | 96.3 | 90 | 1.1 | 101.5 | 1.1 | 1.1 | |

TABLE 2-continued

| | Diagnosis | Aag % | Aact % | Aag/ Aact | Vag % | Vag/ Aag | Vag/ Aact | Category |
|---|---|---|---|---|---|---|---|---|
| | Healthy 3 | 110.5 | 100 | 1.1 | 83.8 | 0.8 | 0.8 | |
| | Healthy 4 | 78.1 | 100 | 0.8 | 46.4 | 0.6 | 0.5 | |
| | Healthy 5 | 89.5 | 100 | 0.9 | 102.2 | 1.1 | 1.0 | |
| | Healthy 6 | 96.4 | 115 | 0.8 | 90.6 | 0.9 | 0.8 | |
| | Healthy 7 | 134.2 | 100 | 1.3 | 87.5 | 0.7 | 0.9 | |
| | Healthy 8 | 90.9 | 100 | 0.9 | 111.3 | 1.2 | 1.1 | |
| | Healthy 9 | 90.1 | 100 | 0.9 | 126.5 | 1.4 | 1.3 | |
| | Healthy 10 | 111.2 | 100 | 1.1 | 115.6 | 1.0 | 1.2 | |
| | Healthy 11 | 110.7 | 120 | 0.9 | 118.2 | 1.1 | 1.0 | |
| | Healthy 12 | 106.5 | 135.5 | 0.8 | 78.7 | 0.7 | 0.6 | |

The measured values obtained from the DIC patients were categorized in accordance with the following indications, based on the measured values obtained from the TTP patients. First, patients in which two or three items from among the following items 1) to 3) apply were categorized into a "group of DIC patients who possibly to suffer from TTP (group A)", and the others were categorized into a "group of DIC patients who do not possibly to suffer from TTP (group B)".

1) The amount (Aag) of the ADAMTS13 antigen is 30% or less.

2) The enzyme activity (Aact) of ADAMTS13 is 15% or less.

3) The ratio (Aact/Aag) of the amount of ADAMTS13 to the ADAMTS13 activity is 2.0 or more. These patient groups (group A and group B) were further categorized into the following three groups:

Group 1: Vag/Aag is 8 or more, and Vag/Aact is 16 or more.

Group 2: Vag/Aag is 8 or less, and Vag/Aact is 16 or more.

Group 3: Other than groups 1 and 2 (i.e., Vag/Aact is less than 16.)

Figure 1:
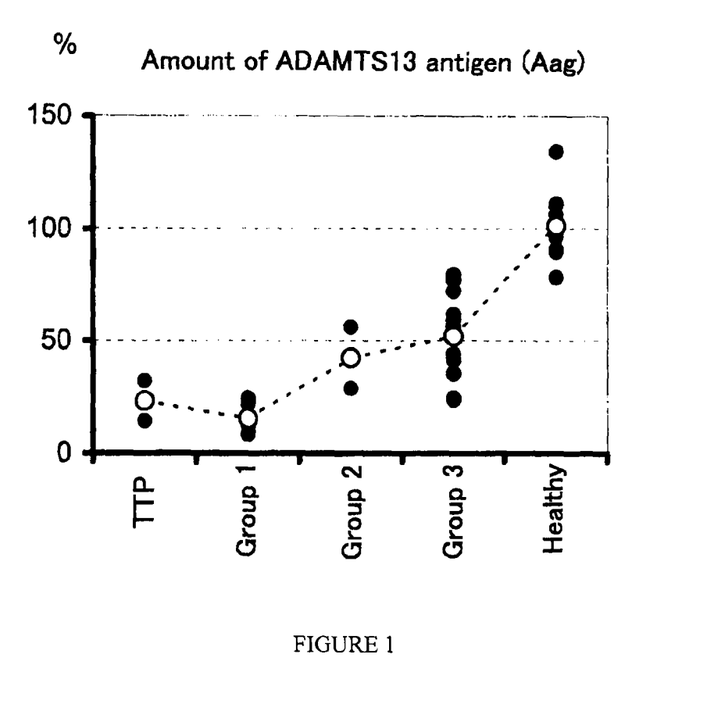
FIG. 1 is a graph showing the result of measuring amounts of the ADAMTS13 antigen (Aag).
Figure 2:
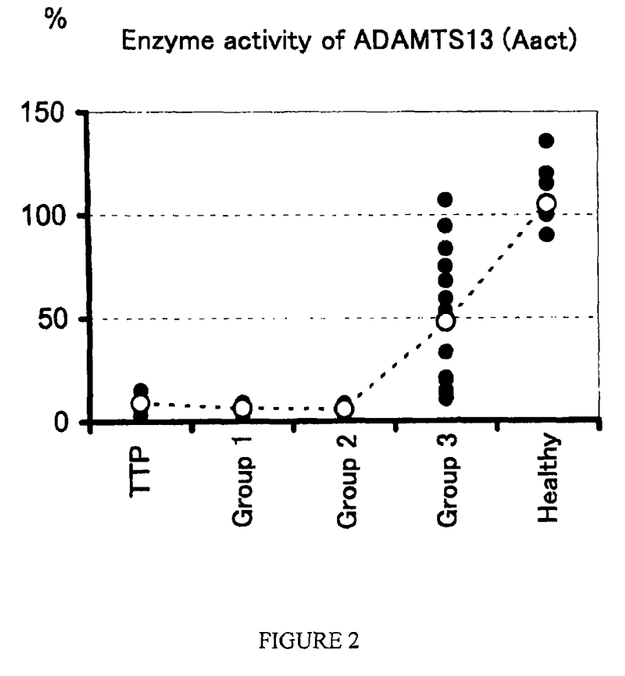
FIG. 2 is a graph showing the result of measuring enzyme activities of ADAMTS13 (Aact).
Figure 3:
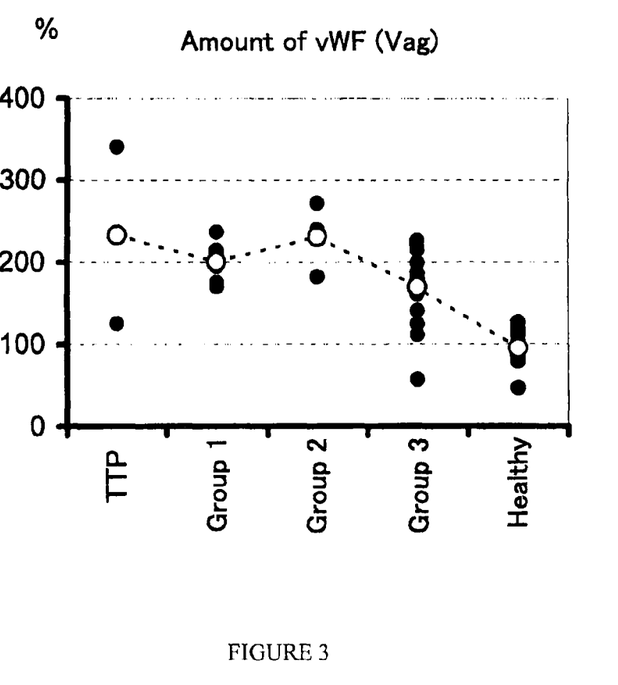
FIG. 3 is a graph showing the result of measuring amounts of the vWF antigen (Vag).

Each patient group was compared with healthy persons, to obtain the results as shown in FIG. 1 to FIG. 3. As shown in the results of the amount (Aag) of the ADAMTS13 antigen, the enzyme activity (Aact) of ADAMTS13, and the amount (Vag) of the vWF antigen, apparent differences between the TTP group and the healthy person group were observed with respect with each marker. Further, the differences between the TTP group and Group 3 were observed with respect to the amount of the ADAMTS13 antigen and the enzyme activity of ADAMTS13, and both groups could be differentiated from each other. Group 2 could be distinguished from the TTP group in the amount of the ADAMTS13 antigen, but could not be distinguished from the TTP group in the enzyme activity of ADAMTS13. With respect to the amount of the vWF antigen, no differences between the TTP group and the DIC groups (Group 1 to Group 3) were observed.

Figure 4:
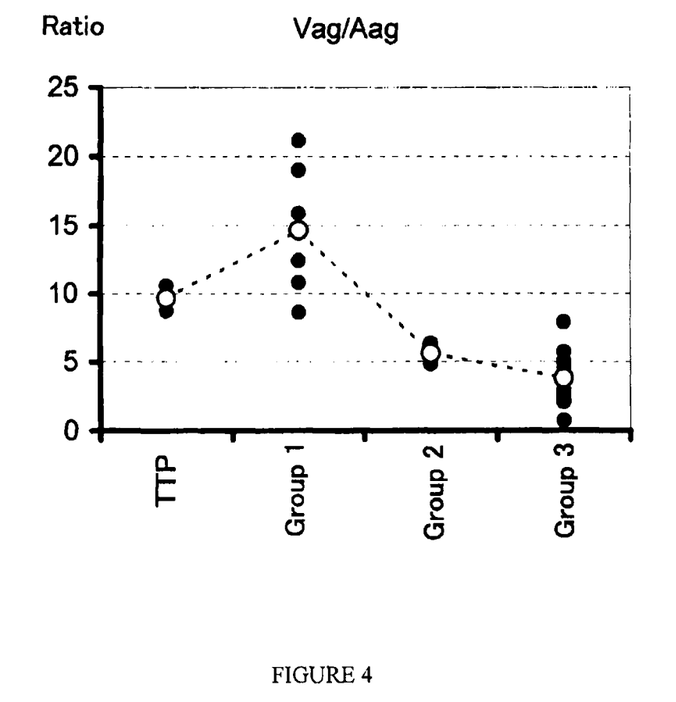
FIG. 4 is a graph showing Vag/Aag.
Figure 5:
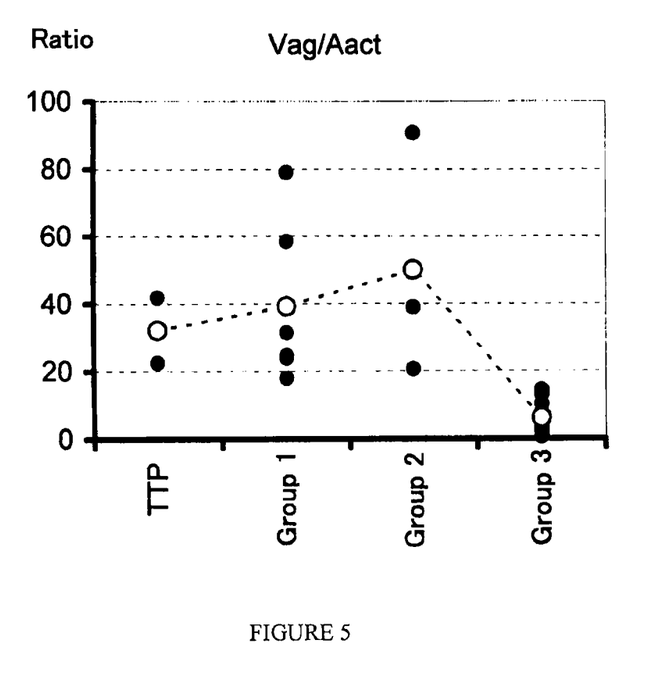
FIG. 5 is a graph showing Vag/Aact.

Based on the above results, the TTP group and the DIC groups categorized into three subgroups were compared in Vag/Aag and Vag/Aact, to obtain the results shown in FIG. 4 and FIG. 5, respectively.

When the ratio (Vag/Aag) of the amount of the vWF antigen to the amount of the ADAMTS13 antigen, or the ratio (Vag/Aact) of the amount of the vWF antigen to the ADAMTS13 activity was used, the median values of Group 1 and Group 2 were less than twice that of the TTP group, but each median of Group 3 exhibited a twofold or greater reduction in comparison with that of the TTP group. It was concluded from this result that Group 3 was a disease apparently different from TTP.

INDUSTRIAL APPLICABILITY

The present invention can be applied to the use for an appropriate treatment of DIC.

Although the present invention has been described with reference to specific embodiments, various changes and modifications obvious to those skilled in the art are possible without departing from the scope of the appended claims.

The invention claimed is:

1. A method for selecting therapy for a patient diagnosed with disseminated intravascular coagulation (DIC), said method comprising:
   collecting a sample of bodily fluid from the patient diagnosed with DIC;
   analyzing the sample for enzyme activity (Aact) of a von Willebrand factor-cleaving protease (ADAMTS13) and the amount (Vag) of von Willebrand factor (vWF);
   calculating a ratio of the amount of vWF to the enzyme activity of ADAMTS13 (Vag/Aact); and
   selecting a therapy for thrombotic thrombocytopenic purpura (TTP) when the calculated ratio (Vag/Aact) value in the DIC patient is half or more of the ratio (Vag/Aact) in known TTP patients.

2. The method of claim 1, wherein the bodily fluid is selected from the group consisting of blood, plasma and serum.

3. The method of claim 1, wherein vWF is immunologically analyzed.

4. The method of claim 1, wherein therapy for thrombotic thrombocytopenic purpura (TTP) is selected when the ratio (Vag/Aact) is 16 or more.

5. A method for selecting a patient to be diagnosed with and treated for thrombotic thrombocytopenic purpura (TTP) from among patients known to have disseminated intravascular coagulation (DIC), said method comprising:
   collecting a sample of bodily fluid from a patient diagnosed with DIC;
   analyzing the sample for enzyme activity (Aact) of a von Willebrand factor-cleaving protease (ADAMTS13) and the amount (Vag) of von Willebrand factor (vWF);
   calculating the ratio of the amount of vWF to the enzyme activity of ADAMTS13 (Vag/Aact); and
   identifying the patient as a patient to be diagnosed with and treated for TTP when the calculated ratio (Vag/Aact) value in the DIC patient is a half or more of the ratio (Vag/Aact) in known TTP patients.

6. The method according to claim 5, wherein the amount of vWF is determined immunologically.

7. The method of claim 5, wherein the bodily fluid is selected from the group consisting of blood, plasma and serum.

8. The method of claim 5, wherein the patient is identified as having TTP when the ratio (Vag/Aact) is 16 or more.

* * * * *